US00PP32714P2

(12) United States Plant Patent
Hansen

(10) Patent No.: US PP32,714 P2
(45) Date of Patent: Dec. 29, 2020

(54) ***SEDUM* PLANT NAMED 'POWDERPUFF'**

(50) Latin Name: ***Sedum* hybrid**
Varietal Denomination: Powderpuff

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 16/873,097

(22) Filed: Jan. 30, 2020

(51) Int. Cl.
*A01H 5/02* (2018.01)
*A01H 6/32* (2018.01)

(52) U.S. Cl.
USPC ..... Plt./479

(58) Field of Classification Search
USPC ..... Plt./479

CPC ... A01H 5/02; A01H 5/00; A01H 5/12; A01H 6/32; A01H 6/328; A01H 6/00
See application file for complete search history.

(56) References Cited

PUBLICATIONS

Germania Seed Walters Gardens, Inc. Bare Root and Plug Perennial Program #49 2020, retrieved from the Internet at https://germaniaseed.com/pdf/2020/749_walters.pdf, pp. 1, 21, 24. (Year: 2020).*

* cited by examiner

*Primary Examiner* — June Hwu

(57) ABSTRACT

A new and distinct ornamental perennial *Sedum* plant named 'Powderpuff' is characterized by tight-forming compact clumps with small-sized, blue-green glaucous foliage and blue-green vertical to arching branched flower stems that resist falling over and opening up in the center of the plant throughout the growing season. Numerous stems produce a multitude of flowers of bright rosy-pink effect completely covering the top of the plant. The new plant is useful for the landscape in containers, as specimens, en masse.

1 Drawing Sheet

Botanical designation: *Sedum* hybrid.
Cultivar denomination: 'Powderpuff'.

STATEMENT REGARDING PRIOR DISCLOSURES UNDER 37 CFR 1.77(B)(6)

The first non-enabling disclosure of the claimed plant, was the photograph and brief description on a website operated by Walters Gardens, Inc. on Feb. 1, 2019. Subsequently the claimed plant was advertised in the "Walters Gardens 19-20 Catalog" distributed beginning May 29, 2019. The claimed plant was first sold privately on Aug. 5, 2019 by Walters Gardens, Inc., who obtained the plant and all information relating thereto, from the inventor. No plants of *Sedum* 'Powderpuff' have been sold in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to a new and distinct cultivar of *Sedum* plant, botanically known as *Sedum* and hereinafter referred to by the cultivar name 'Powderpuff'. There are over 300 recognized species of the genus *Sedum*.

The new *Sedum* plant is a selection of a planned breeding program conducted by the inventor, at a wholesale perennial nursery in Zeeland, Mich., USA.

The new *Sedum* plant was selected as a single seedling from an insect pollinated cross in an isolation block in late summer of 2013 between an unnamed selection of *Sedum tatarinowii* (not patented) as the female or pod parent and the proprietary unreleased hybrid 08-77-94 (not patented) as the male or pollen parent. *Sedum* 'Powderpuff' was assigned the breeder code number 13-40-101 to keep it separated from among thousands of other seedlings of this and other crosses when it progressed through the initial trial phase in the fall of 2015. The selected single seedling clone was originally selected for it strong, healthy, dense growth, colorful foliage and flowers and intermediate traits between the two parents.

Asexual reproduction of *Sedum* 'Powderpuff' by division at a wholesale perennial nursery in Zeeland, Mich., USA since February of 2017 and subsequent vegetative shoot tip cuttings has shown that the unique features of this new *Sedum* plant are stable and reproduced true to type in successive generations.

SUMMARY OF THE INVENTION

Plants of *Sedum* 'Powderpuff' have not been observed under all possible environmental conditions. The phenotype may vary somewhat with variations in environment such as temperature, available water, fertility and light intensity without, however, any variation in genotype.

The following traits have been repeatedly observed and are determined to comprise the unique characteristics of *Sedum* 'Powderpuff' and distinguish it as a new and distinct autumn stonecrop plant unique from all other autumn stonecrop plants known to the inventor:

1. Tight-forming compact domes with vertical to arching stems.

2. Center stems remain erect throughout the growing season produce full habit.
3. Small-sized, blue-green, glaucous foliage.
4. Numerous, branched, blue-green stems produce flower clusters of bright rosy-pink completely cover the top of the plant.

In comparison with the female parent, the new plant has a larger width and height and retains its upright stems better through the entire growing season. The nearest comparison varieties known to the inventor are: 'Crystal Pink' U.S. Plant Pat. No. 22,094, 'Pure Joy' U.S. Plant Pat. No. 24,194, 'Pride and Joy' U.S. Plant patent application Ser. No. 16/602,785 and 'Pillow Talk' U.S. Plant Pat. No. 28,528. Compared with 'Crystal Pink', the new plant is shorter in flower with more flower coverage of a deeper rosy-pink flower, and has larger leaves. 'Pure Joy' is slightly smaller in habit and has lighter pink bicolor flowers. 'Pride and Joy' has slightly taller habit and the flowers are purplish-pink on darker flower stems, and the foliage is more grey-green. 'Pillow Talk' has larger habit and leaves, less stem strength at flowering with flowers are magenta colored. The female parent has thinner more drooping stems, smaller foliage with larger marginal teeth, and the flower is near white to pale pink. The male parent was not maintained in either photographs or plants, so no comparison is possible.

BRIEF DESCRIPTION OF THE PHOTOGRAPHS

The photograph of the new plant demonstrates the unique traits and the overall appearance of *Sedum* 'Powderpuff'. The colors are as accurate as reasonably possible with color reproductions of this type. Variations in ambient light spectrum, source and direction may cause the appearance of minor variation in color. The plants used in the photograph were four-year-old plants grown in an open, full-sun trial garden at a wholesale perennial nursery in Zeeland, Mich. with supplemental water and fertilizer when needed. No plant growth regulators or pinching have been used.

DETAILED BOTANICAL DESCRIPTION

Figure 1:
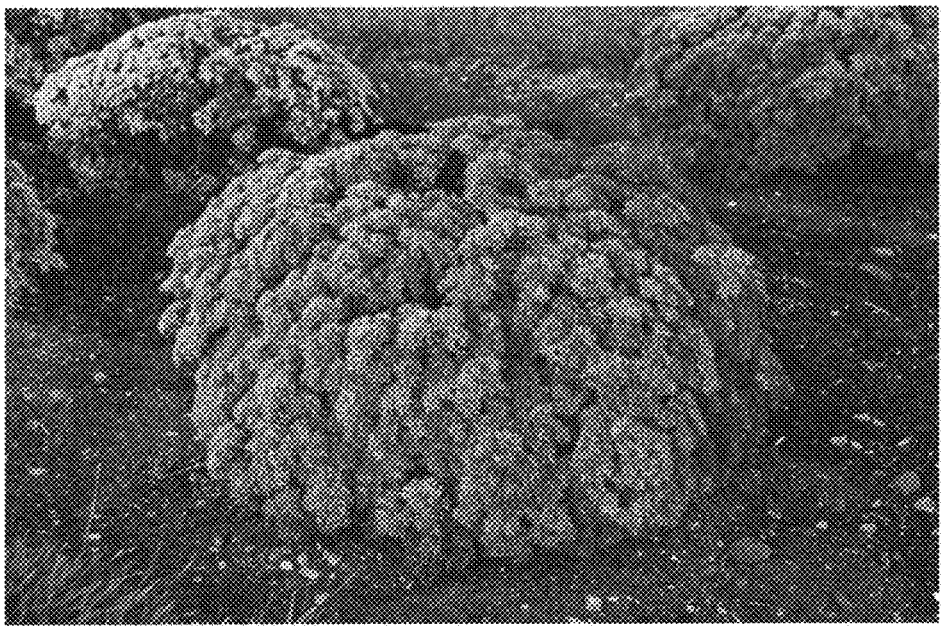
FIG. 1 shows the plant in early stages of flowering with foliage.
Figure 2:
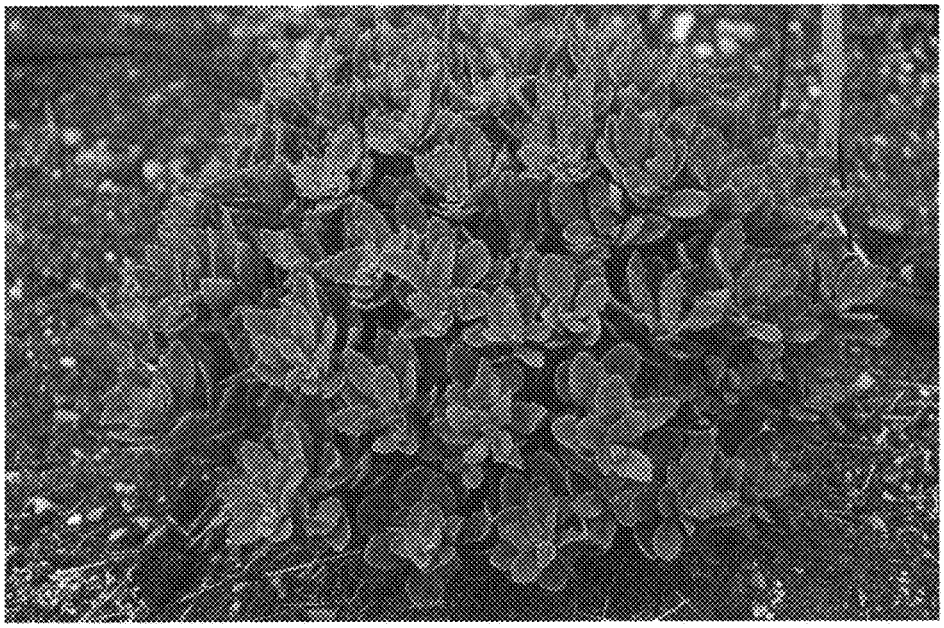
FIG. 2 shows the foliage of the plant in late spring.

The following is a detailed description of four-year-old plants of the new cultivar as grown outdoors in a full sun trial plot at a wholesale nursery in Zeeland, Mich. No plant growth regulators have been used. Plants of the new cultivar have not been tested under all possible conditions. The phenotype may vary with changes in environment, climate, and cultural conditions without change however in the genotype. The color reference is in accordance with the 2015 edition of The Royal Horticultural Society Colour Chart except where general color dictionary terms are used.

Botanical designation: *Sedum* hybrid;

Cultivar denomination: 'Powderpuff';

Parentage: A selection of *Sedum tatarinowii* plant as the female or seed parent; 08-77-94 as the male or pollen parent;

Asexual propagation: Stem tip cuttings and division;

Time to initiate roots: About two weeks;

Time to finish a 3.8 liter flowering container: About three months in the summer from a rooted 2.5 cm plug;

Root description: Thick, fleshy; freely branching; creamy white to light tan in color.

Plant habit: Winter-hardy herbaceous perennial; clumping mound; stems stiff and upright to arching arising from a dense crown; dense and full, not opening in center later in the season; flower heads freely branching;

Growth rate: Moderately vigorous;

Plant size: About 27.0 cm tall and 42.0 cm wide in full flower;

Stems: Terete; glaucous; glabrous; diameter at base average about 5.5 mm and about 21.0 cm long from base to initial branches; 25 internodes per stem, average about 8.4 mm; about 12 stems per plant;

Stem color: Proximally between RHS N138D and RHS 122A, with increasing spotting to moderate blush distally of nearest RHS 187C;

Lateral branches: Glaucous; primary branches to about 7.0 cm long and about 3.0 mm diameter;

Lateral branch color: Proximally between RHS N138D and RHS 122A, with increasing spotting to blush distally of nearest RHS 187C;

Foliage: Ovate; alternate to sub-opposite; simple; smooth; sarcous; glabrous and glaucous on both surfaces; sessile; thick, fleshy and succulent; apex bluntly acute to rounded; base attenuate; margin irregularly and shallowly dentate, 6 to 7 teeth in distal two-thirds of leaf; teeth about 3.0 mm to 8.5 mm apart; decreasing in size distally; attitude outward;

Foliage size: To about 8.5 cm long, 3.4 cm across and 3.0 mm thick; average about 3.8 cm long, 2.1 cm across and 2.0 mm thick;

Foliage color: Adaxial young between RHS 138B and RHS 143C, abaxial young between RHS 138C and RHS 143C; mature adaxial nearest RHS 137B and abaxial nearest RHS N138C;

Petiole: Leaves sessile;

Venation: Palmate, barely distinguishable; slightly raised abaxial;

Vein color: Abaxial and adaxial secondary veins same as surrounding leaf tissue; adaxial midrib lightly nearest RHS 138D, abaxial midrib between RHS 138D and RHS 142D;

Flower: Stellate, actinomophic; pentamerous; persistent; attitude upright to outwardly in terminal compound cymes; size about 11.5 mm across and 7.5 mm deep;

Flower number: About 1,200 to 3,000 flowers per plant;

Fragrance: None detected;

Flowering season: Beginning mid-August in Zeeland, Mich. for about three weeks;

Longevity: Flower cymes remain effective for about three weeks on the plant and one week as cut flowers; individual flowers and calyces persistent and effective for about three weeks;

Flower buds about one day prior to opening: Ellipsoidal; apex acute; base attenuate; about 6.5 mm long and about 2.7 mm diameter near middle;

Flower bud color: Nearest RHS NN74C along petal margin and nearest RHS 65D along petal midrib maculate with nearest RHS NN74C;

Inflorescence: About 7.0 cm tall from first branch and about 9.5 cm across; up to about 200 flowers per inflorescence;

Petals: Typically five, broadly-lanceolate; narrowly acute apex; base fused, truncate; margin entire; glabrous abaxial and adaxial; average about 6.5 mm long and about 2.0 mm across at fusion;

Petal color: Adaxial nearest RHS NN74D with apex nearest RHS NN74A; abaxial distally nearest RHS NN74C, basally between RHS 65D and RHS NN155D; adaxial maturing to nearest RHS NN74D with apex nearest RHS NN74C; abaxial maturing to nearest RHS 75D in longitudinal center and RHS NN74D along margins;

Calyx: With five sepals; campanulate to stellate; about 5.0 mm across and 3.0 mm deep;

Sepals: Linear to lanceolate; narrowly acute apex; fused base; entire margin; glabrous and slightly glaucous both abaxial and adaxial; adpressed to petals, about 2.5 mm long and about 1.0 mm across;

Sepal color: Abaxial and adaxial nearest 138B;

Peduncles: Terete; slightly glaucous, glabrous; stiff and flexible; freely branching; upright to slightly outwardly; with branches to about 45° from perpendicular; about 7.0 cm long and 5.5 mm diameter;

Peduncle color: Nearest RHS 148D maculate with RHS 187C;

Pedicels: Cylindrical; glabrous, slightly glaucous; strong and stiff, yet flexible; about 4.0 mm long and 0.5 mm diameter;

Pedicel color: Blend between RHS N138D and RHS 186C;

Androecium: Typically ten stamens;

*Filaments*.—Cylindrical; outwardly; alternately free to fused to inner corolla in basal 1.0 mm; about 5.5 mm long and about 0.3 mm diameter; color nearest RHS NN74D.

*Anthers*.—Basifixed; longitudinal; ellipsoidal; about 0.7 mm long and 0.5 mm diameter; color nearest RHS N186D.

*Pollen*.—Moderate in quantity; color nearest RHS 160D.

Gynoecium: Typically five; cylindrical, conic in distal one third; about 6.0 mm long and 1.2 mm diameter;

*Style*.—Terete; ellipsoidal, tapering distally and base truncate; about 2.0 mm long and 0.5 mm diameter at point of attachment to ovary; glabrous; color nearest RHS NN74B.

*Stigma*.—Minute, acute; about 0.2 mm diameter and 0.2 mm long; color nearest RHS NN74B.

*Ovary*.—Nearly terete, acutely tapering at apex to style; base truncate; lustrous; about 2.0 mm long and 1.2 mm diameter; color nearest RHS NN74B.

Fruit: Ventrally dehiscent follicle; about 3.5 mm long and 3.2 mm across; color at maturity nearest RHS 177A;

Seed: Sparse; fine; lanceolate; about 1.0 mm long and less than 0.2 mm across; color between RHS 165A and RHS 165B;

Growing conditions: Plants of the new *Sedum* 'Powderpuff' is xeromorphic and grow best with good drainage, full sun and moderate to low fertility. 'Powderpuff' is cold hardy from USDA zones 3 to 9 and has tolerated temperatures of at least 35 degrees C. 'Powderpuff' tolerates heavy rains and wind and is not prone to develop an open center later in the season as many other *Sedum* cultivars do.

Disease and pest resistance: Other pest and disease resistance and tolerance outside that normal for *Sedum* is not known.

It is claimed:

1. A new and distinct perennial *Sedum* plant named 'Powderpuff' as herein described and illustrated.

* * * * *